United States Patent
Zhang et al.

(10) Patent No.: US 10,371,648 B2
(45) Date of Patent: Aug. 6, 2019

(54) RADIOGRAPHY SYSTEMS BASED ON DISTRIBUTED RAY SOURCE

(71) Applicant: NUCTECH COMPANY LIMITED, Beijing (CN)

(72) Inventors: Li Zhang, Beijing (CN); Xin Jin, Beijing (CN); Huaping Tang, Beijing (CN); Qingping Huang, Beijing (CN); Yunda Sun, Beijing (CN); Zhiqiang Chen, Beijing (CN)

(73) Assignee: NUCTECH COMPANY LIMITED, Beijing (CN)

(*) Notice: Subject to any disclaimer, the term of this patent is extended or adjusted under 35 U.S.C. 154(b) by 73 days.

(21) Appl. No.: 15/301,345

(22) PCT Filed: Dec. 14, 2015

(86) PCT No.: PCT/CN2015/097264
§ 371 (c)(1),
(2) Date: Sep. 30, 2016

(87) PCT Pub. No.: WO2016/095775
PCT Pub. Date: Jun. 23, 2016

(65) Prior Publication Data
US 2017/0122884 A1    May 4, 2017

(30) Foreign Application Priority Data
Dec. 17, 2014 (CN) .......................... 2014 1 0787688

(51) Int. Cl.
*G01N 23/00* (2006.01)
*G01N 23/04* (2018.01)
(Continued)

(52) U.S. Cl.
CPC .......... *G01N 23/04* (2013.01); *G01N 23/046* (2013.01); *G01V 5/0041* (2013.01);
(Continued)

(58) Field of Classification Search
CPC ...................................................... G01N 23/04
See application file for complete search history.

(56) References Cited

U.S. PATENT DOCUMENTS 4,736,401 A    4/1988  Donges et al.
9,786,041 B2 * 10/2017  Chen .................... G06T 7/0002
(Continued)

FOREIGN PATENT DOCUMENTS

CN    85107860 A    10/1986
CN    1319759 A     10/2001
(Continued)

OTHER PUBLICATIONS

International Patent Application No. PCT/CN2015/097264; Int'; Search Report; dated Mar. 17, 2016; 2 pages.
(Continued)

*Primary Examiner* — Dani Fox
(74) *Attorney, Agent, or Firm* — BakerHostetler

(57) ABSTRACT

The present disclosure discloses a radiography system including: a ray source, comprising a plurality of X-ray generators which are distributed on one or more planes intersected with a moving direction of an object being inspected; a detector module comprising a plurality of detection units; a data collection circuit; a controller, configured to control at least two X-ray generators of the plurality of X-ray generators in the ray source to generate X-rays alternately such that the object is scanned by the generated X-rays; and control the detector module and the data collection circuit to respectively obtain detection data corresponding to the at least two X-ray generators; and a data processing computer, configured to create images of the object being inspected in view angles of the at least two X-ray generators based on the detection data. The above embodiments may implement a multi-view-angle perspec-
(Continued)

tive imaging system within a single scan plane by utilizing a distributed X-ray source and reuse of the detectors.

10 Claims, 3 Drawing Sheets

(51) Int. Cl.
  *G01N 23/046* (2018.01)
  *G01V 5/00* (2006.01)
(52) U.S. Cl.
  CPC ............... *G01N 2223/3307* (2013.01); *G01N 2223/423* (2013.01); *G01N 2223/643* (2013.01)

(56) References Cited

U.S. PATENT DOCUMENTS

| | | | |
|---|---|---|---|
| 2008/0043917 A1* | 2/2008 | Oreper | G01V 5/0025 378/116 |
| 2009/0010386 A1 | 1/2009 | Peschmann | |
| 2013/0170611 A1 | 7/2013 | Beckmann et al. | |
| 2013/0230139 A1 | 9/2013 | Morton | |
| 2013/0308745 A1 | 11/2013 | Goshen | |
| 2014/0185741 A1 | 7/2014 | Shen et al. | |
| 2014/0233694 A1 | 8/2014 | Wang et al. | |

FOREIGN PATENT DOCUMENTS

| | | |
|---|---|---|
| CN | 1376947 A | 10/2002 |
| CN | 1626039 A | 6/2005 |
| CN | 101231254 A | 7/2008 |
| CN | 101592622 A | 12/2009 |
| CN | 103339657 A | 10/2013 |
| CN | 103462628 A | 12/2013 |
| CN | 203341743 U | 12/2013 |
| CN | 203643369 U | 6/2014 |
| CN | 203772764 U | 8/2014 |
| CN | 203909313 U | 10/2014 |
| CN | 104483711 A | 4/2015 |
| CN | 204422777 U | 6/2015 |
| DE | 10063290 A1 | 9/2001 |
| DE | 112012004856 T5 | 12/2014 |
| WO | WO 2009/115983 A1 | 9/2009 |

OTHER PUBLICATIONS

European Patent Application No. 15869282.2; Extended Search Report; dated Jul. 6, 2018; 7 pages.
German Patent Application No. 112015001147.1; Office Action; dated Nov. 28, 2018; 9 pages.
Johnson; "Dual-Energy CT: General Principles"; American Journal of Roentgenology; Nov. 2012; p. S3-S8.
China Patent Application No. 201410787688.2; Office Action; dated Feb. 25, 2019; 17 pages.

* cited by examiner

RADIOGRAPHY SYSTEMS BASED ON DISTRIBUTED RAY SOURCE

CROSS-REFERENCE TO RELATED APPLICATIONS

This application is a National Stage Application of International Application No. PCT/CN2015/097264, filed on Dec. 14, 2015, entitled "RADIATION IMAGING SYSTEM BASED ON DISTRIBUTED LIGHT SOURCE", which claims priority to Chinese Application No. 201410787688.2 filed on Dec. 17, 2014, incorporated herein by reference in their entirety.

TECHNICAL FIELD

The present disclosure generally relates to radiography, and in particular, to radiography systems based on a distributed ray source.

BACKGROUND

Radiography belongs to inspection means necessary for customs, airports, and railway systems. With a principle of interactions occurring by X-rays penetrating an object, radiography enables content inside a box to be imaged without opening the box, which can effectively identify contrabands such as guns, explosives, drugs in luggage, and have positive effects on protecting citizen's personal and property safety and maintaining social stability.

In the current radiography technology, a main approach of non-destructive testing (NDT) is transmission imaging technology, which utilizes a principle in which X-rays penetrating substance with different densities and materials will generate different attenuations, for implementing non-open-package inspection on freight container, luggage articles. For example, in a patent application with a publication number CN102804326A, the applicant proposed a radiography security inspection system using the X-ray transmission principle, which is mainly constituted by a ray source arranged at one side of an object to be inspected for generating X-rays, a detector module arranged at the other side of the object to be inspected for receiving the ray source, an inspection area for placing the object to be inspected, a data processing unit and a man-machine interaction unit. The above patent also discloses a system and a method for multi-view transmission imaging, which uses a plurality of ray sources and detector modules to form a plurality of scan planes. Respective scan planes scan independently to obtain perspective images of the target in multiple angles, so as to avoid problems of overlapping and difficult recognition of the objects in a single angle view. In addition, dual-energy and multi-energy imaging are also widely used in the transmission imaging technology. For example, a patent application with a publication number CN 102484935A discloses a multi-energy transmission imaging system, which implements energy spectrum decomposition by multiple layers of detector modules corresponding to different energies and by utilizing difference in attenuation capabilities of X-rays with different energies in penetrating substance, so as to obtain estimation on substance atomic number, electron density etc. of the perspective image.

Regarding the security inspection technology, how to identify contrabands in target goods better is core content thereof. Conventional perspective imaging technology improves contraband identification performance mainly by increasing the scan view angle and using dual-energy/multi-energy scan, which has problems as follows.

On one hand, a method of increasing the number of pairs of ray sources and detectors implements perspective scan in different view angles, facilitating to solve the problems of overlapping and difficult recognition for perspective imaging in the single view angle. However, using the scheme of the plurality of ray sources and detectors will considerably increase overall system cost. Moreover, since different pairs of ray sources-detectors need to operate independently, a certain distance interval needs to be maintained between respective scan planes. Therefore, a dual-view-angle/multi-view-angle perspective system always covers a larger area, which limits flexibility and application scope of the system to some extent.

On the other hand, the method of dual-energy/multi-energy imaging may be used for implementing calculation of physical parameters such as atomic number, electron density of substance, facilitating to improve identification capability of contrabands. However, the dual-energy/multi-energy imaging generally uses multiple layers of detectors for implementing differentiated collections of transmitted rays with different energies, which means that the number of detector crystal units and the number of read-out circuits are required to be increased. Considering cost of the detector unit is expensive, using multiple layer detectors will increase the overall system cost, either.

SUMMARY

In view of one or more problems in the prior art, the present disclosure provides a radiography system based on distributed sources.

In one aspect of the present disclosure, a radiography system is provided, including: a ray source including a plurality of X-ray generators which are distributed on one or more planes intersected with a moving direction of an object being inspected; a detector module including a plurality of detection units and configured to receive X-rays transmitting through the object being inspected; a data collection circuit coupled to the detector module and configured to convert a signal generated by the detector module into detection data; a controller connected to the ray source, the detector module and the data collection circuit, and configured to control at least two X-ray generators of the plurality of X-ray generators in the ray source to generate X-rays alternately such that the object is scanned by the generated X-rays as moving of the object, and control the detector module and the data collection circuit to respectively obtain detection data corresponding to the at least two X-ray generators; and a data processing computer configured to create an image of the object being inspected in view angles of the at least two X-ray generators based on the detection data.

According to some embodiments, the detector module includes a low-energy detector and a high-energy detector located behind the low-energy detector.

According to some embodiments, the ray source particularly includes a plurality of carbon nanotube X-ray generators or a plurality of magnetic-confinement X-ray generators.

According to some embodiments, at least some of the plurality of X-ray sources can generate high-energy X-rays and low-energy X-rays in a switching way.

According to some embodiments, the plurality of X-ray generators are arranged on a support in an L shape, an inverted-L shape, a U shape or an arc shape, for emitting the X-rays to the detector module.

According to some embodiments, the ray source includes a first row of X-ray generators and a second row of X-ray generators, which are configured to respectively generate high-energy X-rays and low-energy X-rays in a switching way under control of the controller; and the detector module includes a first row of detectors and a second row of detectors arranged in parallel, which are configured to respectively make response to high-energy X-rays and low-energy X-rays.

According to some embodiments, the plurality of X-ray generators are distributed in pairs, two target points in a pair being close to each other in a spatial distance and having a sequential emitting order, one of which is configured to generate the X-rays using a high voltage with a first energy, and the other of which is configured to generate the X-rays using a high voltage with a second energy.

According to some embodiments, the plurality of X-ray generators are configured to use high voltage with a first energy at one emitting process, and use high voltage with a second energy at the next emitting process, and so on back and forth.

According to some embodiments, at least one of the plurality of X-ray generators are determined to be activated according to spatial resolutions of images to be achieved along a conveying direction under each view angle in connection with a current conveying speed and/or a signal-to-noise ratio of the images.

According to some embodiments, at least one of the plurality of X-ray generators are manually determined to be activated according to a projection angle to be viewed; or an X-ray generator in a best perspective view angle is determined according to a shape and a size of a target object.

According to some embodiments, the radiography system further includes: an object border detection apparatus, configured to detect the object border of the object before the object passes through a scan plane, wherein X-ray generator are selected according to the detected object border such that the generated X-ray covers the target object completely.

The above embodiments implement a multi-view-angle perspective imaging system within a single scan plane by utilizing a distributed X-ray source and reuse of the detectors.

In the above embodiments, cost of the detector module may be reduced effectively. In addition, a single-plane design enables the overall volume of the system to be kept in a smaller level, facilitating to improve mobility and flexibility of the system. Such a scheme can improve overall competitiveness of the system effectively, and implement multi-view-angle perspective imaging with lower cost and higher efficiency.

BRIEF DESCRIPTION OF THE DRAWINGS

In order to illustrate the objects, technical solutions and advantages of the present disclosure more clearly, particular embodiments of the present disclosure will be described in detail with reference to the drawings, in which.

DETAILED DESCRIPTION

Figure 1:
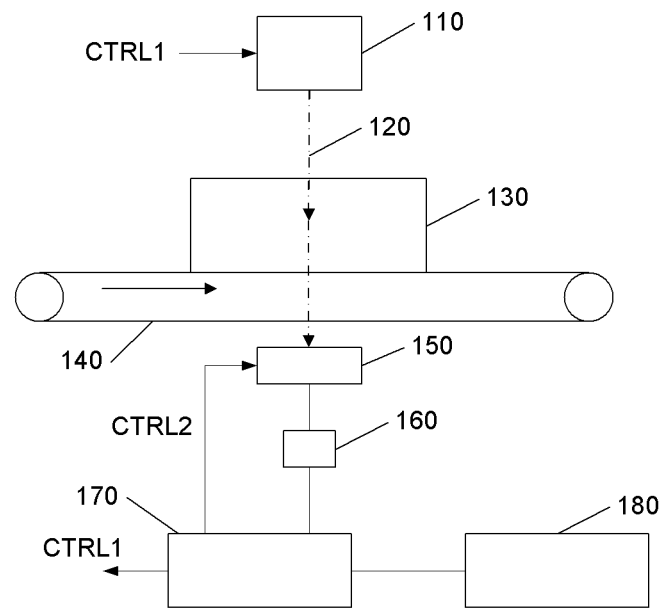
FIG. 1 shows a schematic structure diagram of a radiography system according to an embodiment of the present disclosure.

Hereinafter, particular embodiments of the present disclosure will be described in detail. It should be noted that the embodiments described here are illustrated only for explanation, but not for limitations on the present disclosure. In the following description, a great amount of particular details are illustrated for providing thorough understanding on the present disclosure. However, it is obvious for the skilled in the art that these particular details are not necessarily used for implementing the present disclosure. In other instances, well-known structures, materials or methods are not described in detail to avoid from obscuring the present disclosure.

Throughout the specification, the reference to "one embodiment," "an embodiment," "one example" or "an example" means that the specific features, structures or properties described in conjunction with the embodiment or example are included in at least one embodiment of the present disclosure. Therefore, the phrases "in one embodiment," "in an embodiment," "in one example" or "in an example" presented in various positions throughout the specification may not necessarily refer to the same embodiment or example. Furthermore, specific features, structures or properties may be combined into one or more embodiments or examples in any appropriate combination and/or sub-combination. Moreover, it should be understood for those skilled in the art that the term "and/or" used herein means any and all combinations of one or more listed items.

According to an embodiment of the present disclosure, a radiography system based on distributed ray sources is proposed for the problems in the prior art, which can implement multi-view-angle scan in a simpler structure. For example, a ray source includes a plurality of X-ray generators. The plurality of X-ray generators are distributed on one or more planes intersected with a moving direction of an object being inspected. A detector module includes a plurality of detection units, which can receive X-rays transmitting through the object being inspected. A data collection circuit is coupled to the detector module, and converts a signal generated by the detector module into detection data. A controller is connected to the ray source, the detector module and the data collection circuit, and controls at least two X-ray generators of the plurality of X-ray generators in the ray source to generate X-rays alternately such that the object is scanned by the generated X-rays as moving of the object. In addition, the controller controls the detector module and the data collection circuit to respectively obtain detection data corresponding to the at least two X-ray generators. A data processing computer creates an image of the object being inspected in view angles of the at least two X-ray generators based on the detection data. According to the above embodiment, the multi-energy and multi-view-angle scan may be implemented in a scan plane.

According to some embodiments, a pulse distributed X-ray source module may be used. The pulse distributed X-ray source may implement pulse-type emitting, so as to emit X-rays only within a sampling period of the detector and to stop emitting the X-rays outside the sampling period of the detector. As such, different ray sources may rapidly emit X-rays alternately, implementing continuous perspective scans in different view angles. The ray source in one view angle only may be activated at each emitting. Thus, the rays from different view angles are independent of each other, and do not interfere with each other.

Accordingly, one detector module is used for detecting rays from different X-ray sources, thus the detector must guarantee during collection that every collection only collects the rays emitted from one ray source at some time, i.e., collection of the detector and exposure of the ray source are synchronized. As such, since there is only one scan plane and the detector is effectively reused for imaging in different view angles, the cost of the detector module may be effectively reduced, and price competitiveness of the system may be improved. Also, the single-plane design enables the overall volume of the system to be kept in a smaller level, facilitating to improve mobility and flexibility of the system.

In addition, the number of ray sources, i.e., the number of view angles of imaging, required to be used is determined during scanning according to different scan parameters, and respective ray sources are switched rapidly according to a specified emitting order during scanning. For example, the distributed X-ray source scan may be implemented base on technology such as carbon nanotube, magnetic-confinement etc., i.e., the X-ray beams being generated from a plurality of different spatial locations may be implemented on one ray source module. Especially, the distributed ray source based on the carbon nanotube technology may implement X-ray source points with great amount and dense distribution, implementing perspective imaging in many view angles. Therefore, the distributed ray source with the carbon nanotube may implement such a case in which the number of source points on the system is larger than the number of imaging view angles, while the device cost is barely increased.

As such, since all of ray sources correspond to the same detector module, after the system completes the collection, the collected data must be divided according to the ray source numbers (i.e., the projection view angles), and then the data from the same ray source module (i.e., in the same perspective view angle) are combined, so as to obtain a perspective image of this ray source (i.e., in this view angle); and after the images in respective view angles are obtained, the multi-view-angle imaging is finally achieved. In other words, since the detector module is reused by respective ray sources during the scan process of the system, the number of collections of images in each of the view angles is 1/N of the total number of the collections, where N is the number of projection view angles. This means that in a case that the total number of collections are identical, image quality in respective view angles will be reduced as the number of the view angles is increased, mainly in that the number of sampling in a moving direction of the belt is reduced, i.e., spatial resolution in this direction will become worse. Therefore, an appropriate number of view angles may be determined according to actual scan parameters or actual requirements.

According to some embodiments, the detector module may use a single-energy module, or A) may implement multi-energy detection in a dual-layer/multi-layer form, in which case different layers have different ray energy responses, and a filtering sheet may be installed between the layers according to actual requirements to adjust energy spectrum of incident rays; B) may implement dual-energy/multi-energy detection in a dual-row/multi-row form, in which case different rows have different ray energy responses, and filtering sheets may be installed in front of respective rows according to actual requirements to adjust energy spectrum of incident rays.

In some embodiments, the positions of all of source points of the ray source may be distributed in a scan plane which is perpendicular to the moving direction of the belt, or may be distributed in the moving direction of the belt, or may be randomly distributed in a 3D space, as long as it can be guaranteed that the ray beams from respective source points can be received by the detector module.

In addition, the system may implement dual-energy/multi-energy energy spectrum by the ray source for the purpose of dual-energy/multi-energy scan, besides implementing the dual-energy/multi-energy detection on the detector module. For example, a single-energy detector may be used for the dual-energy imaging, and the following schemes may be applied to the ray source module: A) the source points of the ray source are distributed in pairs, two target points in a pair being close to each other in a spatial distance and having a sequential emitting order, one of which generates the X-rays using a high voltage with a first energy, and the other of which generates the X-rays using a high voltage with a second energy which is different from the first energy; B) respective source points of the ray source use high voltage with the first energy at some emitting time, and use high voltage with the second energy at a next emitting time, and so on back and forth.

During scanning, only activated source points in the ray source module participate in scanning and imaging, and the number of the activated source points may be determined: A) according to spatial resolutions of images to be achieved along a moving direction of the belt under each view angle in connection with a current speed of the belt; in a case of a constant spatial resolution, if the speed of the belt is higher, only a fewer number of source points are activated; and if the speed of the belt is lower, a larger number of source points are activated; B) specified manually, in which case every emitting process and emitting strength of each source point may be determined according to the number of the source points and the speed of the belt as well as a signal-to-noise ratio of the images.

In addition, during scanning, only the activated source points in the ray source module participate in scanning and imaging, and the numbers of the activated source points may be determined A) by specified manually according to the projection angle need to be viewed; B) by determining a best perspective view angle according to a shape and a size of a target object, e.g., for a sheet-like target object (such as a box), selecting an angle in which an average distance of transmitting through the object by the rays is smaller for performing the perspective imaging.

In some embodiments, the distributed ray sources of the system are distributed along two sides adjacent to a scan channel (in a cross section perpendicular to the moving direction of the object), and the detectors are distributed along additional two sides adjacent to the scan channel. Since respective source points of the ray source are located close enough to the channel so that A) the rays emitted by parts of the source points cannot cover the whole channel completely in their scan plane due to limitation of the opening angle of the emitted ray beams; or B) even if a ray beam of some ray covers the whole scan channel in its scan plane, there is still possibility that the detector cannot receive all of rays penetrating the scan channel, due to effects of the position of the ray source and the arrangement of the detector. In this case, an object border detection apparatus may be arranged in the system, and may detect a border of the object before the object passes the scan plane.

As such, during scanning of the system, the source points for scanning the current object may be selected A) dependent on the number of the source points need to be activated which is obtained by the system using the method of determining the number of the source points as previously discussed; B) according to the object border detected by the system for enabling the complete coverage on the target object.

In the above embodiments, the multi-view-angle perspective imaging system within the single scan plane may be implemented by utilizing the distributed X-ray sources and reuse of the detectors. As such, cost of the detector module may be reduced effectively. In addition, a single-plane design enables the overall volume of the system to be kept in a smaller level, facilitating to improve mobility and flexibility of the system. The present disclosure can improve overall competitiveness of the system effectively, and implement multi-view-angle perspective imaging with lower cost and higher efficiency.

FIG. 1 shows a schematic structure diagram of a radiography system according to an embodiment of the present disclosure. The radiography system as shown in FIG. 1 includes a bearing mechanism 140, such as a belt, for bearing an object 130 being inspected to move on; a distributed X-ray source 110; a detector module 1150; a collection circuit 160; a controller 170 and a data processing computer 180 etc. The ray source 110 includes a plurality of X-ray generators, which are distributed on one or more planes intersected with the moving direction of the object 130 being inspected.

As shown in FIG. 1, the bearing mechanism 140 bears the luggage 130 being inspected to go through a scan area between the ray source 110 and the detector 150. In some embodiments, the detector 150 and the collection circuit 160 are a detector and a data collector in an integrated module structure, e.g., a plurality of rows of detectors, for detecting the rays transmitting through an article being inspected so as to obtain the analog signal, and for converting the analog signal to the digital signal, thereby outputting projection data of the object being inspected for the X-rays. The controller 170 controls various components of the whole system to work synchronously. The data processing computer 180 processes data collected by the data collector, creates images of the object, and outputs the result.

According to the embodiment, the detector 150 and the collection circuit 160 are used for obtaining transmission data of the object 130 being inspected. A data amplifying circuit is included in the collection circuit 160, and may work in a (current) integrated manner or a pulse (counting) manner. Data output cable of the collection circuit 150 is connected to the controller 170 and the data processing computer 180, and the collected data are stored in the computer 180 according to a trigger command.

In some embodiments, the detector module 150 includes a plurality of detection units for receiving the X-rays which transmit through the object being inspected. The data collection circuit 160 is coupled to the detector module 150 for converting a signal generated by the detector module 160 to detection data. The controller 170 is connected via a control line CTRL11 to the ray source 110 and is connected via a control line CTRL12 to the detector module which is in turn connected to the data collection circuit, so as to control at least one X-ray generator of the ray source to generate the X-rays which are emitted for transmitting through the object being inspected as the object being inspected moves. In addition, the controller 170 controls the detector module 150 and the data collection circuit 160 to obtain the detection data. The data processing computer 180 creates the images of the object being inspected in the view angles of the at least two X-ray generators based on the detection data.

Figure 2:
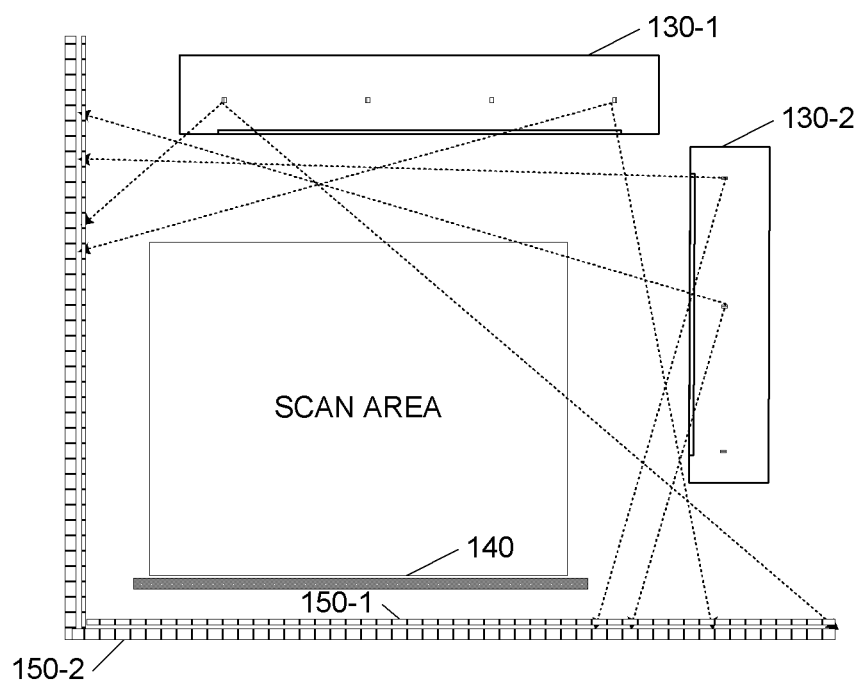
FIG. 2 is a schematic view of an operation process of a radiography system according to an embodiment of the present disclosure.

FIG. 2 is a schematic view of an operation process of a radiography system according to an embodiment of the present disclosure. The ray sources 130-1 and 130-2 for generating the X-ray beams include a plurality of cathodes for generating free electrons and corresponding anode source points. The detector includes at least one row of detectors for detecting the rays from the ray source, and forming different X-ray perspective images respectively according to different source points. The conveying mechanism carries the object being inspected to pass through the system. The data processing unit processes data collected by the detector, and generates the perspective image and performs automatic identification on contrabands.

Figure 3:
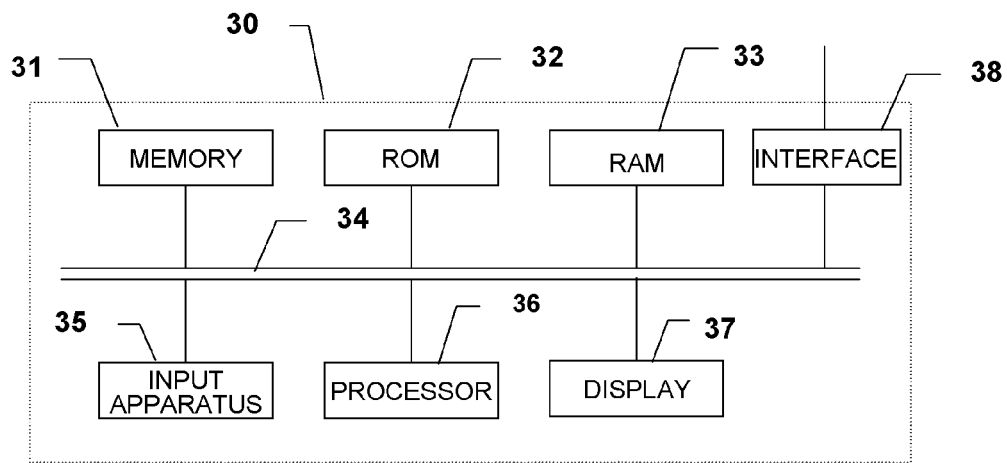
FIG. 3 shows a schematic diagram of an internal structure of a computer for image processing in the embodiment as shown in FIG. 1.

FIG. 3 shows a schematic structure diagram of the data processing computer 180 as shown in FIG. 1. As shown in FIG. 3, the data collected by the collection circuit 160 are stored in a memory 31 via an interface unit 38 and a bus 34. Configuration information and program of the computer data processor are stored in a Read-Only memory (ROM) 32. A Random Access memory (RAM) 33 is used for temporarily storing various data during operation of a processor 36. In addition, the memory 31 further stores computer program for data processing. The internal bus 34 is connected to the above memory 31, the ROM 32, the RAM 33, an input apparatus 35, the processor 36, a display apparatus 37 and the interface unit 38.

After the user inputs an operation command by the input apparatus 35 such as a keyboard and a mouse, instruction codes of the computer program instructs the processor 36 to perform predetermined data processing algorithm; after a data processing result is obtained, the result is displayed on the display apparatus 37 such as LCD display, or is output directly in a form of hard copy such as printing.

In the embodiment, the plurality of source points of the ray sources 130-1 and 130-2 and the detector constitute the scan plane together, in which the ray source includes multiple ray source points, and working voltages of different source points are identical, and working currents of different source points are identical; and the detector is single-row and dual-layer detector, in which a layer firstly penetrated by the rays is low-energy detector unit 150-1 which mainly detects low-energy rays, and a layer secondly penetrated by the rays is high-energy detector unit 150-2 which mainly detects high-energy rays.

In the embodiment, the conveying mechanism is a conveyer belt system arranged at the bottom of the scan plane, which is responsible for carrying the object being inspected to pass through the scan plane. In the embodiment, only the activated source points scan the object, and when the object being inspected passes through the scan plane, respective activated source points emit the rays circularly and ensure that only one source point is in the emitting state at one instant, and at the same time, the detector array performs collection synchronously in cooperation with the source points, so as to obtain projection data of different source points at respective emitting times.

In the embodiment, the data processing computer 180 processes the sampled data in real time, and display the processing result on the display. When the object being inspected leaves the scan plane, the scan data of the object are processed to obtain the perspective images scanned by different source points, images related to atomic numbers are obtained by dual-energy decomposition technology, substance classification and contraband identification are performed, pseudo-color tinting is performed on the images according to the classification and the identification results to form the dual-energy perspective image which is in turn displayed on the display.

Figure 4:
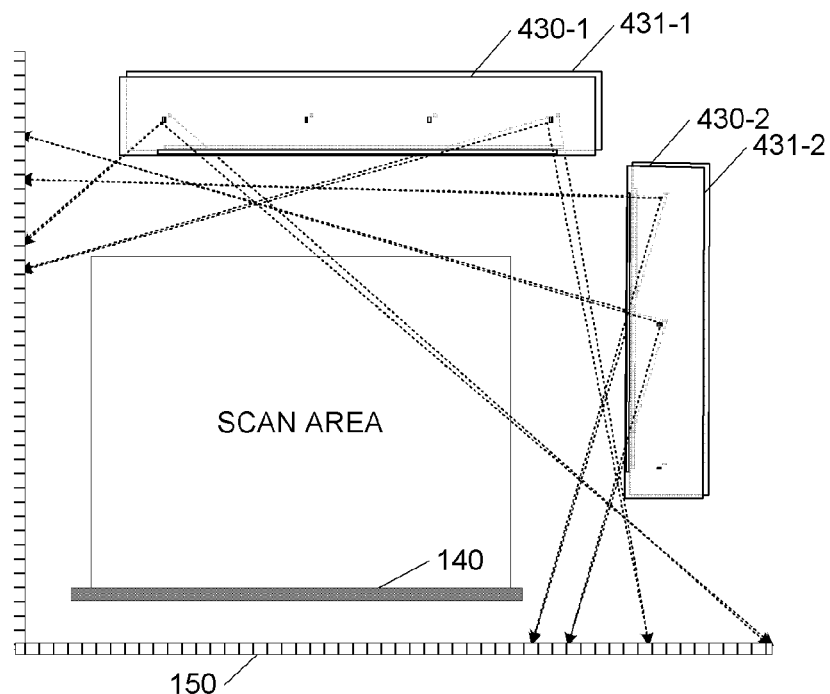
FIG. 4 is a schematic view of an operation process of a radiography system according to another embodiment of the present disclosure.

FIG. 4 is a schematic view of an operation process of a radiography system according to another embodiment of the present disclosure. Difference between the embodiment as shown in FIG. 4 and the embodiment as shown in FIG. 2 consists in that the scan plane is constituted by a single-energy detector and two sets of X-ray source modules 430-1, 431-1 and 430-2, 431-2 in parallel with the channel direction, in which the voltage of one set of X-ray source modules is lower than the other set, and the voltages and the currents are consistent in respective sets of X-ray source modules. During scanning, all of the source points emit the rays sequentially, but the source points corresponding to the two sets of X-ray source modules emit their rays sequentially.

Figure 5:
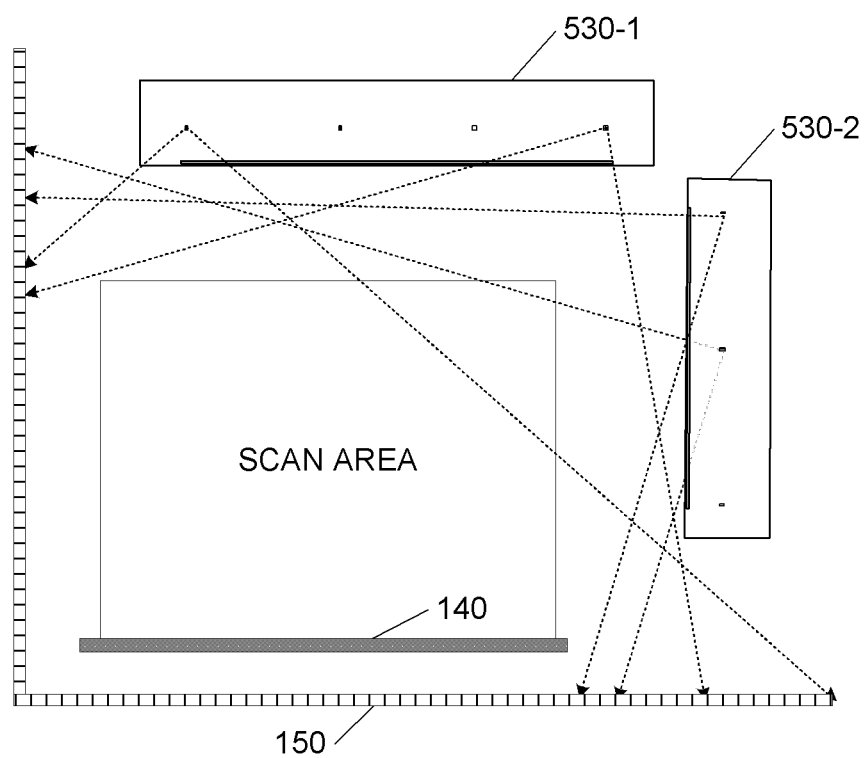
FIG. 5 is a schematic view of an operation process of a radiography system according to yet another embodiment of the present disclosure.

FIG. 5 is a schematic view of an operation process of a radiography system according to yet another embodiment of the present disclosure. Difference between the embodiment as shown in FIG. 5 and the embodiment as shown in FIG. 4 consists in that the scan plane is constituted by a single-energy detector and one set of X-ray source modules 530-1 and 530-2 in parallel with the channel direction, in which each source point of the X-ray source module may have two (or multiple) kinds of voltages and implement dual-energy (or multi-energy) scan. During scanning, all of the source points emit their rays sequentially, respective source points continuously emit its rays twice (or several times) with different energies, and the detector performs collections twice (or several times) synchronously in cooperation with the source points.

Although inverted-L shape of a two-segment type is used in the ray source, other distribution ways may be easily contemplated by the skilled in the art. For example, the plurality of X-ray sources may be arranged on a support in an L shape, a U shape or an arc shape, for emitting the X-rays to the detector module.

In the above embodiments, the multi-view-angle perspective imaging system within the single scan plane may be implemented by utilizing the distributed X-ray sources and reuse of the detectors. In the above embodiments, cost of the detector module may be reduced effectively. In addition, a single-plane design enables the overall volume of the system to be kept in a smaller level, facilitating to improve mobility and flexibility of the system. Such a scheme can improve overall competitiveness of the system effectively, and implement multi-view-angle perspective imaging with lower cost and higher efficiency.

The above detailed description has already set forth numerous embodiments of the method and device for estimating the weight information of the object to be inspected with reference to the diagrams, flow charts, and/or examples. In the case where the diagrams, flow charts, and/or examples comprise one or more functions and/or operations, one skilled in the art should appreciate that each function and/or operation in the diagrams, flow charts, or examples may be implemented by various structures, hardware, software, firmware or any combination thereof either alone and/or in any combination. In an embodiment, several parts of the subject matter described in the embodiments of the present disclosure may be implemented by Application Specific Integrated Circuit (ASIC), Field Programmable Gate Array (FPGA), Digital Signal Processor (DSP), or any other integrated form. However, one skilled in the art should appreciate that some aspects of the embodiment disclosed herein may be partially or wholly implemented in an integrated circuit effectively, implemented as one or more computer programs running on one or more computers (for example, one or more programs running on one or more computer systems), implemented as one or more programs running on one or more processors (for example, one or more programs running on one or more micro-processors), implemented as firmware, or substantially any combination thereof, and one skilled in the art is capable to design the circuit and/or write software and/or firmware code. Further, one skilled in the art would appreciate that the mechanism of the subject matter of the present disclosure may be distributed in various forms of program products, and the exemplary embodiments of the subject matter of the present disclosure may be applicable irrespective of the specific types of signal carrier media for distribution. Examples of the signal carrier media comprise but not limited to: a recordable medium such as floppy disk, hard drive, compact disk (CD), digital versatile disk (DVD), digital tape, computer memory, etc.; and a transmission medium, such as digital and/or analog communication medium (for example, optical fiber, waveguide, wired communication link, wireless communication link, etc.)

Although the present disclosure is already described with reference to several typical embodiments, it is to be appreciated that the terms used herein are illustrative and exemplary, rather than limiting. Since the present disclosure may be practice in multiple forms without departing from the spirit or essence, it is to be noted that the above embodiments are not limited to any previously described details and shall be interpreted broadly within the spirit and scope defined by the claims. Therefore, all changes and variations fall into the scope of the claims or their effectives shall be embraced by the claims.

We claim:

1. A radiography system comprising:
a ray source comprising a plurality of X-ray generators which are distributed on one or more planes intersected with a moving direction of an object being inspected;
a detector module comprising a plurality of detection units and configured to receive X-rays transmitting through the object being inspected;
a data collection circuit coupled to the detector module and configured to convert a signal generated by the detector module into detection data;
a controller connected to the ray source, the detector module and the data collection circuit, and configured to control at least two X-ray generators of the plurality of X-ray generators in the ray source to generate X-rays alternately such that object is scanned by the generated X-rays as moving of the object, and control the detector module and the data collection circuit to respectively obtain detection data corresponding to the at least two X-ray generators;
a data processing computer configured to create images of the object being inspected in view angles of the at least two X-ray generators based on the detection data;
wherein the ray source implements pulse-type emitting so as to emit X-rays only within a sampling period of the detector module and stop emitting the X-rays outside the sampling period of the detector module; wherein the detector module detects rays from different X-ray generators in the ray source, and in each collection process, rays emitted from only one X-ray generator are collected by the detector module at a time; and
wherein the radiography system further comprises an object border detection apparatus, the object border detection apparatus configured to detect an object border of the object before the object passes through a scan plane; wherein an X-ray generator is selected according to the detected object border such that the generated X-ray covers the object completely.

2. The radiography system according to claim 1, wherein the detector module comprises a low-energy detector and a high-energy detector located behind the low-energy detector.

3. The radiography system according to claim 1, wherein the ray source comprises a plurality of carbon nanotube X-ray generators or a plurality of magnetic-confinement X-ray generators.

4. The radiography system according to claim 1, wherein at least some of the plurality of X-ray generators are configured to generate high-energy X-rays and low-energy X-rays in a switching way.

5. The radiography system according to claim 1, wherein the plurality of X-ray generators are arranged on a support in an L shape, an inverted-L shape, a U shape or an arc shape, for emitting the X-rays to the detector module.

6. The radiography system according to claim 1, wherein the ray source comprises a first row of X-ray generators and a second row of X-ray generators, which are configured to respectively generate high-energy X-rays and low-energy X-rays in a switching way under control of the controller; and the detector module comprises a first row of detectors and a second row of detectors arranged in parallel, which are configured to respectively make response to high-energy X-rays and low-energy X-rays.

7. The radiography system according to claim 1, wherein the plurality of X-ray generators are distributed in pairs, two target points in a pair being close to each other in a spatial distance and having a sequential emitting order, one of which is configured to generate the X-rays using a high voltage with a first energy, and the other of which is configured to generate the X-rays using a high voltage with a second energy.

8. The radiography system according to claim 1, wherein the plurality of X-ray generators are configured to use high voltage with a first energy at one emitting process, and use high voltage with a second energy at the next emitting process, and so on back and forth.

9. The radiography system according to claim 1, at least one of the plurality of X-ray generators is determined to be activated according to spatial resolutions of images to be achieved along a conveying direction under each view angle in connection with a current conveying speed and/or a signal-to-noise ratio of the images.

10. The radiography system according to claim 1, at least one of the plurality of X-ray generators is manually determined to be activated according to a projection angle to be viewed; or an X-ray generator in a best perspective view angle is determined according to a shape and a size of a target object.

* * * * *